United States Patent
Nguyen et al.

(10) Patent No.: US 9,433,771 B2
(45) Date of Patent: Sep. 6, 2016

(54) QUICK DISCONNECT FLUID CONNECTOR

(75) Inventors: Nick N. Nguyen, Silverado, CA (US); Walter Francovich, Pierrefonds (CA); Philippe Conseil, Roxboro (CA)

(73) Assignee: ETHICON, INC., Somerville, NJ (US)

( * ) Notice: Subject to any disclaimer, the term of this patent is extended or adjusted under 35 U.S.C. 154(b) by 896 days.

(21) Appl. No.: 12/998,458

(22) PCT Filed: Oct. 5, 2009

(86) PCT No.: PCT/US2009/059521
§ 371 (c)(1),
(2), (4) Date: Aug. 29, 2011

(87) PCT Pub. No.: WO2010/045052
PCT Pub. Date: Apr. 22, 2010

(65) Prior Publication Data
US 2012/0007352 A1    Jan. 12, 2012

Related U.S. Application Data (60) Provisional application No. 61/196,715, filed on Oct. 13, 2008.

(51) Int. Cl.
*A61M 39/12* (2006.01)
*A61L 2/18* (2006.01)
*A61L 2/26* (2006.01)
*A61M 39/10* (2006.01)

(52) U.S. Cl.
CPC .............. *A61M 39/12* (2013.01); *A61L 2/18* (2013.01); *A61L 2/26* (2013.01); *A61L 2202/123* (2013.01); *A61L 2202/24* (2013.01); *A61M 2039/1027* (2013.01)

(58) Field of Classification Search
CPC ................ A61M 2039/1027; A61M 39/12; A61L 2202/123
USPC .......................................................... 285/317
See application file for complete search history.

(56) References Cited

U.S. PATENT DOCUMENTS

| 1,492,521 | A | 4/1924 | Meyer |
| 2,996,317 | A | 8/1961 | Kibbie et al. |
| 3,682,503 | A | 8/1972 | Bloom |
| 3,719,375 | A | 3/1973 | Nordin |

(Continued)

FOREIGN PATENT DOCUMENTS

| CN | 1872349 A | 12/2006 |
| EP | 1055860 A2 | 11/2000 |

(Continued)

OTHER PUBLICATIONS

International Search Report for International Application No. PCT/US2009/059521 mailed Feb. 22, 2010 3 pages.

(Continued)

*Primary Examiner* — James Hewitt (57) ABSTRACT

Coupling arrangements and connectors for establishing a substantially fluid-tight removable connection between a plurality of fluid ports or channels in a medical device such as, an endoscope. Various embodiments of the connectors may be coupled to a plurality of fluid conduits that may be attached to a decontamination or reprocessing device used to flow fluid through corresponding channels in the medical device during the decontamination process.

20 Claims, 10 Drawing Sheets

(56) References Cited

U.S. PATENT DOCUMENTS

| | | | |
|---|---|---|---|
| 3,899,200 A | | 8/1975 | Gamble |
| 4,116,476 A | | 9/1978 | Porter et al. |
| 4,483,510 A | * | 11/1984 | Palau et al. ............ 251/149.6 |
| 4,637,378 A | | 1/1987 | Sasa |
| 4,753,268 A | | 6/1988 | Palau |
| 4,981,469 A | | 1/1991 | Whitehouse et al. |
| 5,167,220 A | | 12/1992 | Brown |
| 5,234,417 A | | 8/1993 | Parks et al. |
| 5,534,228 A | | 7/1996 | Wesseler |
| 5,749,829 A | | 5/1998 | Yokoi et al. |
| 5,806,832 A | * | 9/1998 | Larbuisson ............ 251/149.6 |
| 5,911,443 A | | 6/1999 | LeQuere |
| 6,095,971 A | | 8/2000 | Takahashi |
| 6,158,829 A | | 12/2000 | Nielsen |
| 6,273,478 B1 | | 8/2001 | Benett et al. |
| 6,454,314 B1 | | 9/2002 | Grosspietsch et al. |
| 6,485,684 B1 | | 11/2002 | Mapson et al. |
| 6,840,548 B2 | * | 1/2005 | Lacroix ....................... 285/308 |
| 6,958,017 B1 | | 10/2005 | Toombs, Jr. |
| 6,986,736 B2 | | 1/2006 | Williams et al. |
| 7,152,621 B1 | | 12/2006 | Huetinck |
| 7,153,296 B2 | | 12/2006 | Mitchell |
| 7,316,425 B2 | | 1/2008 | Poder |
| 7,561,473 B2 | | 7/2009 | Mokhlesi et al. |
| 7,604,262 B2 | | 10/2009 | Elflein et al. |
| 7,686,761 B2 | | 3/2010 | Jackson et al. |
| 7,753,415 B2 | * | 7/2010 | Tiberghien et al. ......... 285/316 |
| 7,828,336 B2 | | 11/2010 | Gammons |
| 7,837,646 B2 | | 11/2010 | Eidinger et al. |
| 7,887,102 B2 | * | 2/2011 | Tiberghien et al. ......... 285/317 |
| 7,901,350 B2 | | 3/2011 | Yamazaki |
| 8,113,548 B2 | | 2/2012 | Gunderson |
| 8,146,883 B2 | | 4/2012 | O'Hara |
| 2008/0065000 A1 | | 3/2008 | Bidinger et al. |
| 2011/0298169 A1 | | 12/2011 | Nguyen et al. |
| 2011/0298209 A1 | | 12/2011 | Nguyen et al. |

FOREIGN PATENT DOCUMENTS

| | | |
|---|---|---|
| EP | 1433410 A1 | 6/2004 |
| EP | 1728466 A2 | 12/2006 |
| EP | 1762172 A2 | 3/2007 |
| EP | 1762172 A2 | 3/2007 |
| GB | 2226861 A | 7/1990 |
| GB | 2226861 A | 7/1990 |
| JP | 2-209690 A | 8/1990 |
| JP | 2-225898 A | 9/1990 |
| JP | 5-49596 A | 3/1993 |
| JP | 7-67938 A | 3/1995 |
| JP | 8-112247 A | 5/1996 |
| JP | 2000-070218 A | 3/2000 |
| JP | 2000-70218 A | 7/2000 |
| JP | 2002-071073 A | 3/2002 |
| JP | 2002-71073 A | 3/2002 |
| JP | 2004-202247 A | 7/2004 |
| JP | 2005-58258 A | 3/2005 |
| JP | 2006-55325 A | 3/2006 |
| JP | 2006-149556 A | 6/2006 |
| JP | 2007-289723 A | 11/2007 |
| WO | WO 2006/062912 A1 | 6/2006 |

OTHER PUBLICATIONS

International Preliminary Report on Patentability for International Application No. PCT/US2009/059521 issued Apr. 19, 2011, 7 pages.
International Search Report for International Application No. PCT/US2009/059517 issued Dec. 23, 2009.
International Preliminary Report on Patentability for International Application No. PCT/US2009/059517 issued Apr. 19, 2011.
International Search Report for International Application No. PCT/US2009/059525 issued May 17, 2010.
International Preliminary Report on Patentability for International Application No. PCT/US2009/059525 issued Apr. 19, 2011.

* cited by examiner

QUICK DISCONNECT FLUID CONNECTOR

CROSS-REFERENCE TO RELATED APPLICATIONS

This application is a National Stage entry of International Application No. PCT/US2009/059521, entitled QUICK DISCONNECT FLUID CONNECTOR, filed on Oct. 5, 2009, which claims the benefit of U.S. Provisional Patent Application No. 61/196,715, entitled QUICK DISCONNECT FLUID CONNECTOR, filed on Oct. 13, 2008.

FIELD OF THE INVENTION

The present invention generally relates to connectors and, more particularly, to fluid connectors used in connection with reprocessing or decontamination systems for medical devices having one or more internal passageways that need to be cleaned and disinfected after use such as, for example, endoscopes.

BACKGROUND

In various circumstances, an endoscope can include an elongate portion, or tube, having a distal end which can be configured to be inserted into the body of a patient and, in addition, a plurality of channels extending through the elongate portion which can be configured to direct water, air, and/or any other suitable fluid into a surgical site. In some circumstances, one or more channels in an endoscope can be configured to guide a surgical instrument into the surgical site. In any event, an endoscope can further include a proximal end having inlets in fluid communication with the channels and, in addition, a control head section having one or more valves, and/or switches, configured to control the flow of fluid through the channels. In at least one circumstance, an endoscope can include an air channel, a water channel, and one or more valves within the control head configured to control the flow of air and water through the channels.

Decontamination systems can be used to reprocess previously-used medical devices, such as endoscopes, for example, such that the devices can be used once again. During the decontamination process of an endoscope, the air and water channels within the endoscope can be evaluated in order to verify that the channels are unobstructed. A variety of decontamination systems exist for reprocessing endoscopes. In general, such systems may include at least one rinsing basin, in which an endoscope that is to be cleaned and/or disinfected can be placed. The basin is commonly supported by a housing that supports a system of lines, pumps and valves for the purpose of feeding a cleaning and/or disinfecting agent to an endoscope which has been placed in a rinsing basin. Such devices also include a collection of lines, hoses, conduits or pipes that are coupled to the pumps and corresponding ports in the endoscope by releasable connectors. Such connectors must achieve a fluid-tight seal while attached to the endoscope, yet be easily releasable at the conclusion of the process. If the connector fails to achieve a fluid-tight seal, all of the endoscope's lumens may never receive the disinfecting liquid medium to ensure that the inner surfaces of the lumen have been adequately disinfected.

While a variety of disconnectable fluid connectors have been designed over the years to couple the fluid-supplying lines from a reprocessing system to an endoscope lumen port, such connectors at times may not achieve a fluid-tight seal with the port or such connectors may be difficult to connect and detach from the port or ports. Other connectors are somewhat complex and may be difficult to manufacture and may easily be inadvertently disconnected from their respective ports on the endoscope.

Accordingly, there is a need for disconnectable connector for coupling fluid supply conduits to corresponding port or ports of an endoscope that may address some of the shortcomings of prior connectors.

The foregoing discussion is intended only to illustrate some of the shortcomings present in the field of the invention at the time, and should not be taken as a disavowal of claim scope.

SUMMARY

In at least one form of the invention, there is provided a connector for simultaneously coupling first and second fluid coupling ports protruding from an endoscope to corresponding first and second fluid conduits, respectively. In various embodiments, the connector may include a housing that has a first fluid passage that extends therethrough such that it is in fluid communication with the first fluid conduit. The housing may further have a second fluid passage that extends therethrough and is in fluid communication with the second fluid conduit. Various embodiments may further include a latch slide that may be movably supported within the housing and may be selectively movable between a latched position wherein the latch slide retainingly engages at least one retention feature on the first fluid coupling port such that the first fluid coupling port is retained in substantially fluid-tight registration with the first fluid passage in the housing and the second fluid coupling port is simultaneously retained in substantially fluid-tight registration with the second fluid passage in the housing. The latch slide may be further selectively moved to an unlatched position wherein the connector may be detached from the first and second fluid coupling ports. The connector may further comprise a biaser that is supported within the housing to bias the latch slide into the latched position.

In connection with other general aspects of various embodiments of the present invention, there is provided a coupling arrangement for conveying fluids from a reprocessing device through corresponding channels in an endoscope. In various embodiments, the coupling arrangement may comprise a first fluid coupling port that protrudes from the endoscope and is in fluid communication with a first channel in the endoscope. The first fluid coupling port may have at least one retention feature protruding therefrom. The coupling arrangement may further include a first fluid conduit that has a first supply end that operably communicates with a first source of fluid associated with the reprocessing device. The first fluid conduit further has a first discharge end. In addition, the coupling arrangement may further include a second fluid coupling port that protrudes from the endoscope and is in fluid communication with a second channel in the endoscope. A second fluid conduit may have a second supply end that operably communicates with a second source of fluid associated with the reprocessing device. The second fluid conduit may have a second discharge end. In various embodiments, the coupling arrangement may further comprise a housing that has a first fluid passage that extends therethrough which is in fluid communication with the first discharge end of the first fluid conduit and a second fluid passage that extends therethrough which is in fluid communication with the second discharge end of the second fluid conduit. A latch slide may be movably supported within the housing such that it may be selectively movable between a latched position wherein the latch slide retainingly engages the at least one retention feature on the first fluid coupling port such that the first fluid coupling port is retained in substantially fluid-tight registration with the first fluid passage in the housing and the second fluid coupling port is simultaneously retained in substantially fluid-tight registration with the second fluid passage in the housing and an unlatched position wherein the connector may be detached from the first and second elongate coupling members. Various embodiments of the coupling arrangement may further comprise a biaser that is supported within the housing to bias the latch slide into the latched position.

This Summary is intended to briefly outline certain embodiments of the subject invention. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

The following U.S. patent applications, which are each herein incorporated by reference and which are each being contemporaneously filed with the present application are commonly owned by the Assignee of the present application:

(1) U.S. patent application Ser. No. 13/089,109, entitled Fluid Connector For Endoscope Reprocessing System, now abandoned; and (2) U.S. patent application Ser. No. 13/089,106, entitled Endoscope Channel Separator, now abandoned.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 2:
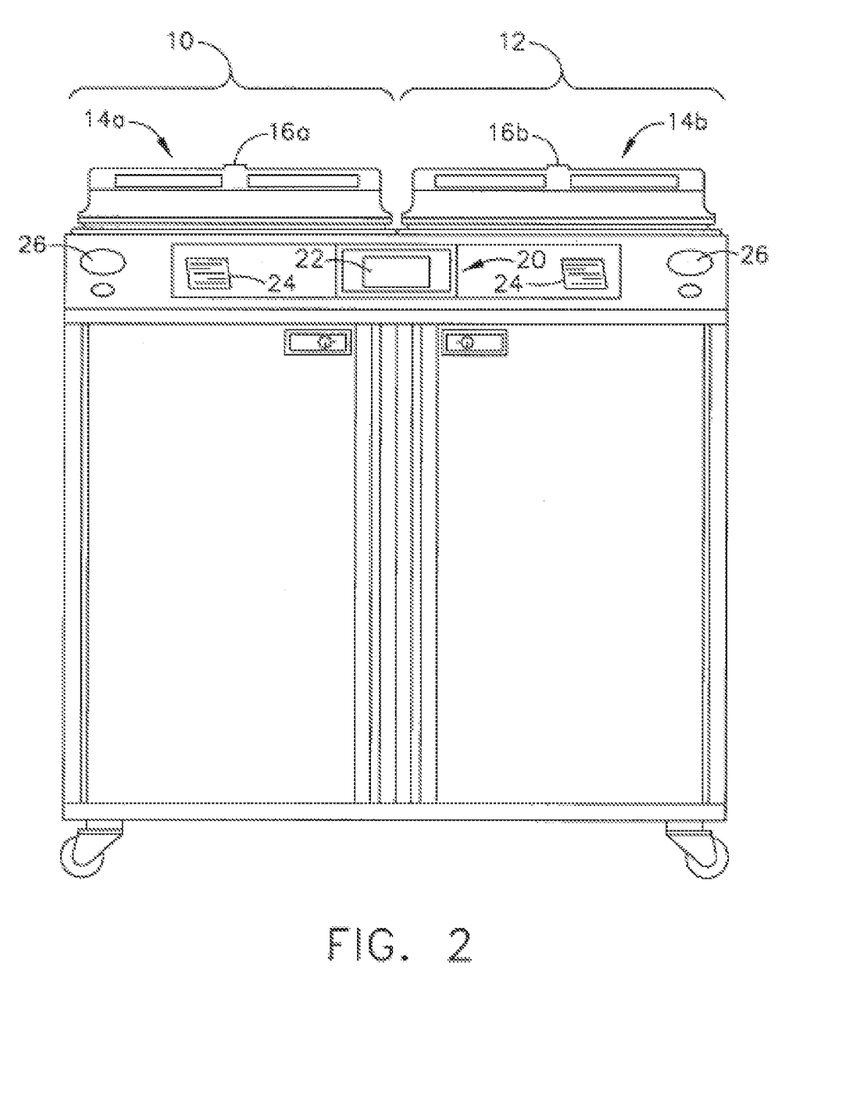
FIG. 2 is a front elevational view of a decontamination apparatus.

One embodiment of a decontamination apparatus is depicted in FIG. 2 which may be configured for decontaminating endoscopes and/or other medical devices. A variety of different systems and devices for decontaminating and reprocessing medical devices such as, for example, endoscopes are known in the art. Accordingly, the scope of protection afforded to the various connector arrangements of the present invention should not be limited to a particular processor or decontamination apparatus configuration.

In various arrangements, the decontamination apparatus can generally include one or more stations for decontaminating a medical device. In at least one arrangement, the decontamination apparatus can include a first station 10 and a second station 12 which can be at least substantially similar in all respects to provide for the decontamination of a medical device in series or two different medical devices simultaneously. In at least one arrangement, first and second decontamination basins, or chambers, 14a, 14b can receive the contaminated devices, wherein each chamber 14a, 14b can be selectively sealed by a lid 16a, 16b, respectively, preferably in a microbe-blocking relationship to prevent the entrance of microbes into the chambers 14a, 14b during the operation of the decontamination apparatus. In various arrangements, the lids can include a microbe removal or HEPA air filter, for example, for providing a flow of vented air therethrough.

A control system 20 can include one or more microcontrollers, such as a programmable logic controller (PLC), for example, for controlling the operation of the decontamination apparatus. Although one control system 20 is shown herein as controlling both decontamination stations 10, 12, each station 10, 12 can include a dedicated control system. In various arrangements, the decontamination apparatus can further include at least one visual display 22 configured to display decontamination parameters and machine conditions to an operator and, in addition, at least one printer 24 configured to print a hard copy output of the decontamination parameters which can be filed in a record-keeping system and/or attached to the decontaminated device or its storage packaging. In at least one arrangement, for example, the visual display 22 can be combined with a touch screen input device to facilitate the use of control system 20. In various arrangements, a keypad or the like can be provided for the input of decontamination process parameters and otherwise controlling the decontamination apparatus. Gauges, such as gauges 26, for example, can include pressure meters and/or any other suitable measuring device which can provide digital and/or analog output of decontamination or medical device leak testing data. Various leak testing devices and methods are disclosed in U.S. Pat. No. 6,986,736, entitled AUTOMATED ENDOSCOPE REPROCESSOR CONNECTION INTEGRITY TESTING, which issued on Jan. 17, 2006, the entire disclosure of which is hereby incorporated by reference herein.

Figure 3:
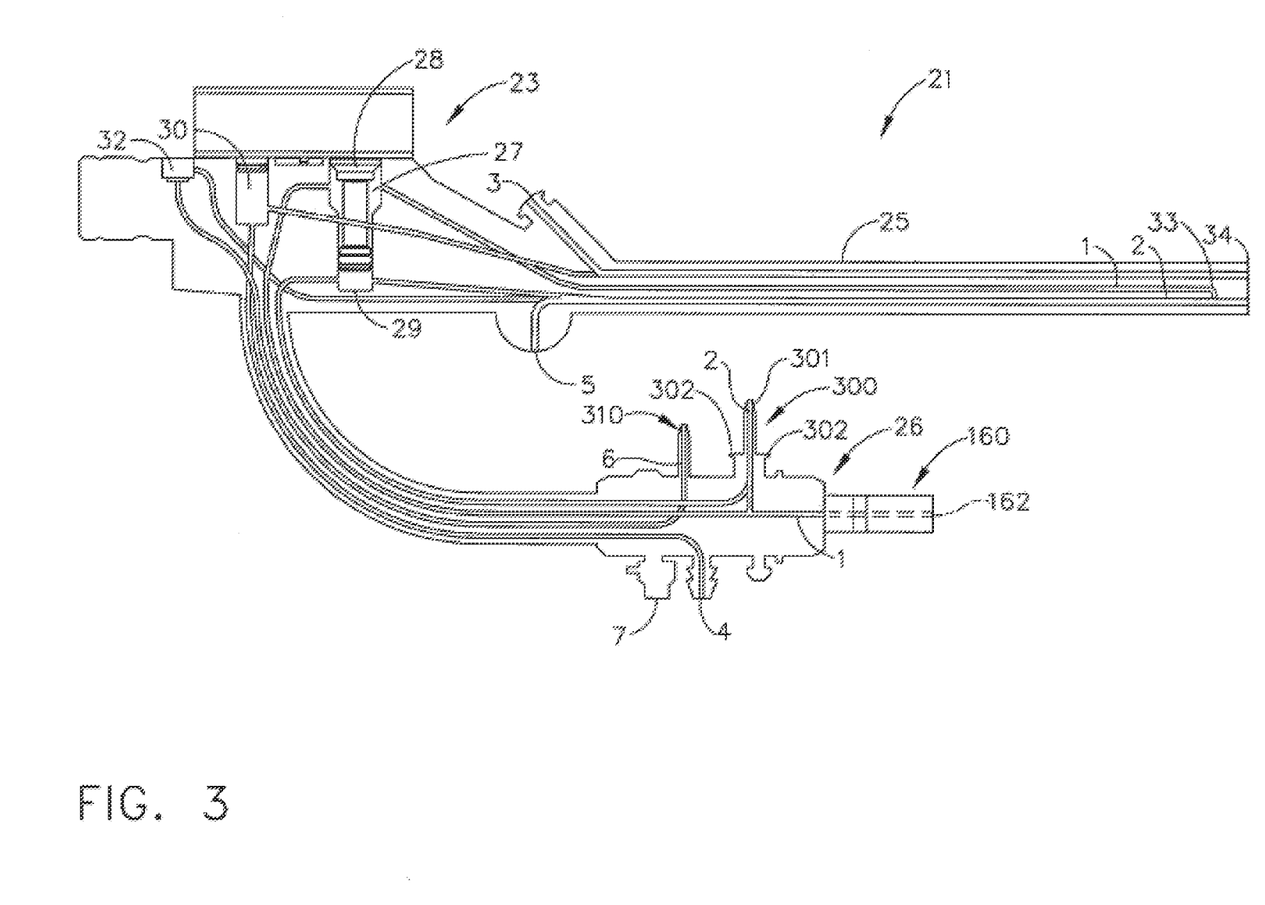
FIG. 3 is an elevational depiction of an endoscope, showing various channels lumens and passageways therein.

In various embodiments, referring to FIG. 3, an endoscope, such as endoscope 21, for example, can include elongate portion, or insertion tube 25 which can be configured to be inserted into the body of a patient through a trocar, for example. In at least one embodiment, endoscope 21 can further include proximal portion, or light guide section, 26, control head section 23, and one or more channels, or lines, for conveying a fluid. More particularly, an endoscope can include one or more channels extending therethrough which can be configured to convey a fluid, such as water, air, and/or carbon dioxide, for example, into a surgical site. As used herein, the term "fluid" may comprise liquid materials such as water, decontamination and sterilization liquids, etc., as well as materials in a vapor or gaseous state, such as, for example, air, carbon dioxide and various other gases. As used herein, the term "in fluid communication" means that a fluid-carrying or fluid-transporting member (e.g., pipe, hose, conduit, channel, etc.) is coupled to another fluid-carrying or fluid-transporting member so as to permit the fluid to flow or otherwise migrate from one member to the other.

Referring to FIG. 3, endoscope 21 can include a first channel 1 which is in fluid communication with a lumen 162 in a fluid coupling member 160 that may, for example, protrude from proximal end 26. Channel 1 may extend, for example, through at least a portion of control head section 23 and elongate portion 25, and to an outlet at distal end 34. In various embodiments, channel 1 can be configured to convey air to the surgical site, for example. Endoscope 21 can also include second channel 2 which can be configured to convey water from an inlet at proximal end 26, for example, through at least a portion of control head section 23 and elongate portion 25, and to an outlet at distal end 34. An endoscope 21 can further include additional channels, such as channel 4, for example, which can be configured to provide a vacuum, or suction, to a surgical site. An endoscope 21 can also include channel 6 for providing carbon dioxide. In at least one embodiment, an endoscope 21 can further include biopsy channel 3, for example, which can be configured to receive a surgical instrument therein such that the surgical instrument can be guided into the surgical site through the endoscope. In some embodiments, an endoscope 21 can further include a channel, such as channel 5, for example, which can be configured to convey a highly-pressurized jet of water that is discharged from distal end 34. In at least one embodiment, proximal end 26 can further include leak test connector 7 which can be configured to introduce a pressurized fluid and/or vacuum into the endoscope in order to inspect for leaks between the channels, for example.

In various embodiments, still referring to FIG. 3, control head section 23 can include valve chamber 32 which can be configured to receive a valve element therein such that the valve element can control the flow of carbon dioxide, for example, through the endoscope. In at least one embodiment, the valve element can comprise a stopcock, for example, which can be configured to allow carbon dioxide to flow through channel 6 when the stopcock is in a first, or open, position and prevent, or at least substantially prevent, the flow of carbon dioxide through channel 6 to distal end 34 when the stopcock is rotated into a second, or closed, position. Similarly, in various embodiments, control head section 23 can include valve chamber 30 which can be configured to receive a valve element therein which can be configured to control whether vacuum, or suction, can be communicated to distal end 34 through channel 4. In various embodiments, as discussed in greater detail below, control head section 23 can include a valve chamber, such as valve chamber 27, for example, comprising a first portion 28 in fluid communication with channel 1 and, in addition, a second portion 29 in fluid communication with channel 2. For the purposes of this application, any number of valves, channels, and/or any other suitable devices can be deemed to be in fluid communication with each other if a fluid can flow between the devices whether by pressure differential, gravity feed, and/or any other suitable manner.

In various embodiments, valve chamber 27 can be configured to receive a valve element having a seal configured to sealingly separate valve chamber 27 into portions 28 and 29. In at least one embodiment, the seal can be configured such that air flowing through channel 1 does not flow into, or at least substantially flow into, second portion 29, for example. Similarly, the seal can also be configured such that water flowing through channel 2 does not flow into, or at least substantially flow into, first portion 28. In various embodiments, although not illustrated, such a valve element can assist in sealingly separating two or more channels such that fluids flowing therethrough can be discharged from separate orifices in the distal end of an endoscope. In at least one alternative embodiment, referring to FIG. 3, channels 1 and 2 can be placed in fluid communication with one another at a location, such as location 33, for example, which is downstream from valve chamber 27 such that the air and water flowing through channels 1 and 2, respectively, can be discharged from the endoscope through a common orifice.

Figure 4:
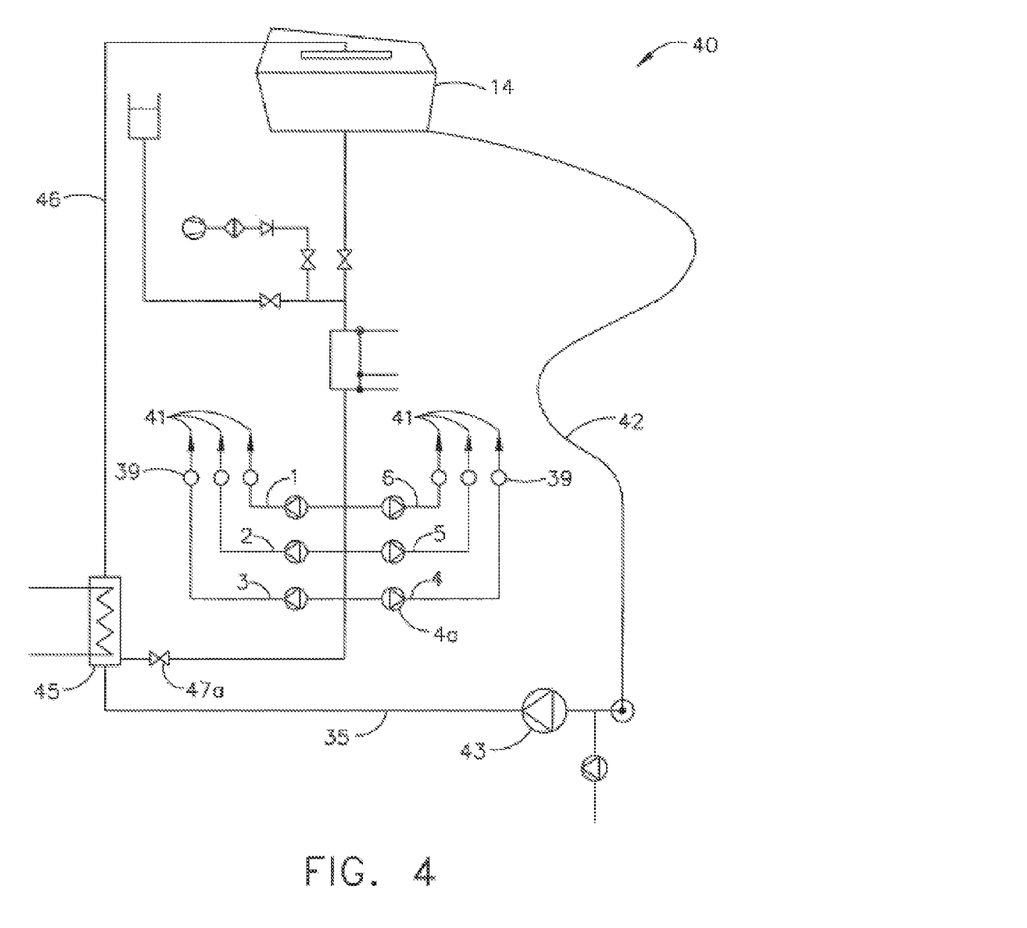
FIG. 4 is a schematic representation of a decontamination system that may be employed in connection with various embodiments of the present invention.
Figure 5:
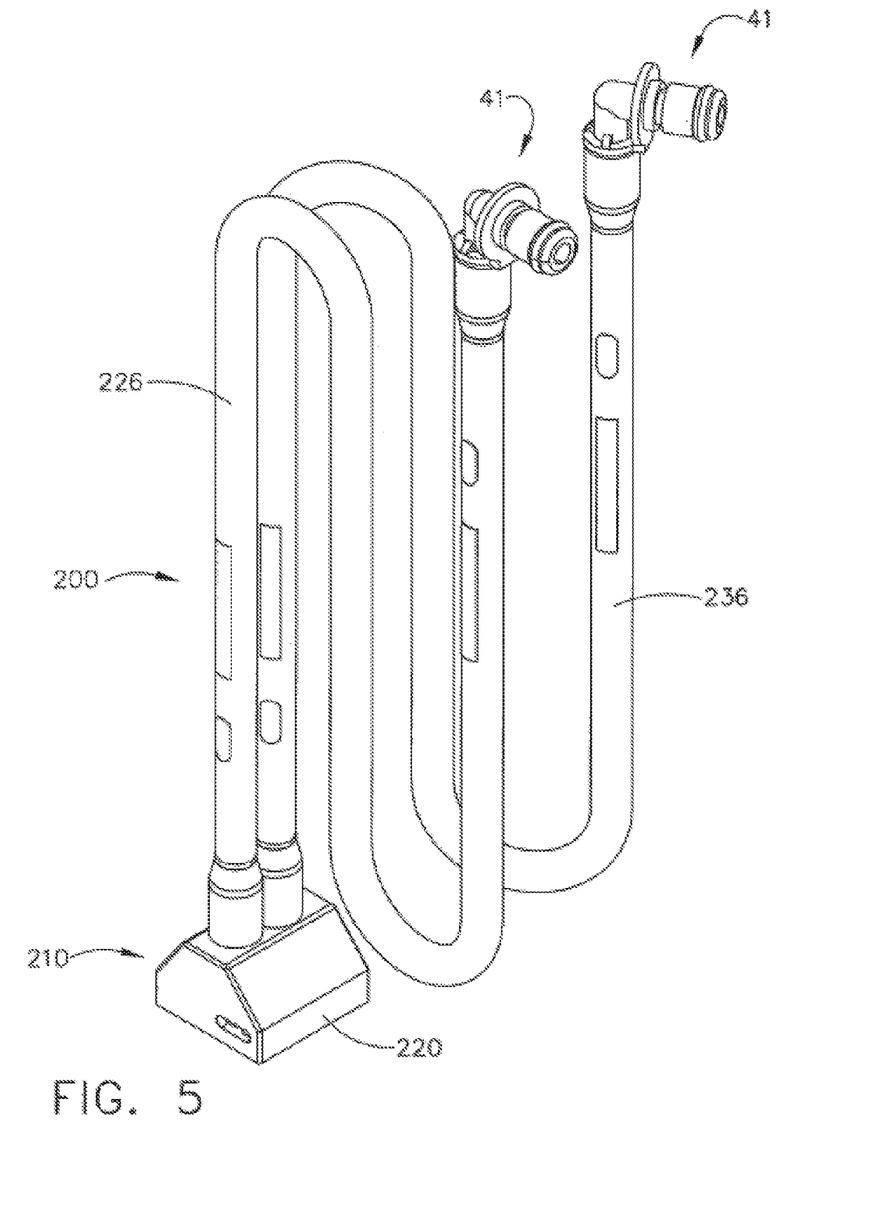
FIG. 5 is a perspective view of a coupling arrangement of various embodiments of the present invention for simultaneously coupling to ports of a medical instrument to fluid conduits.
Figure 6:
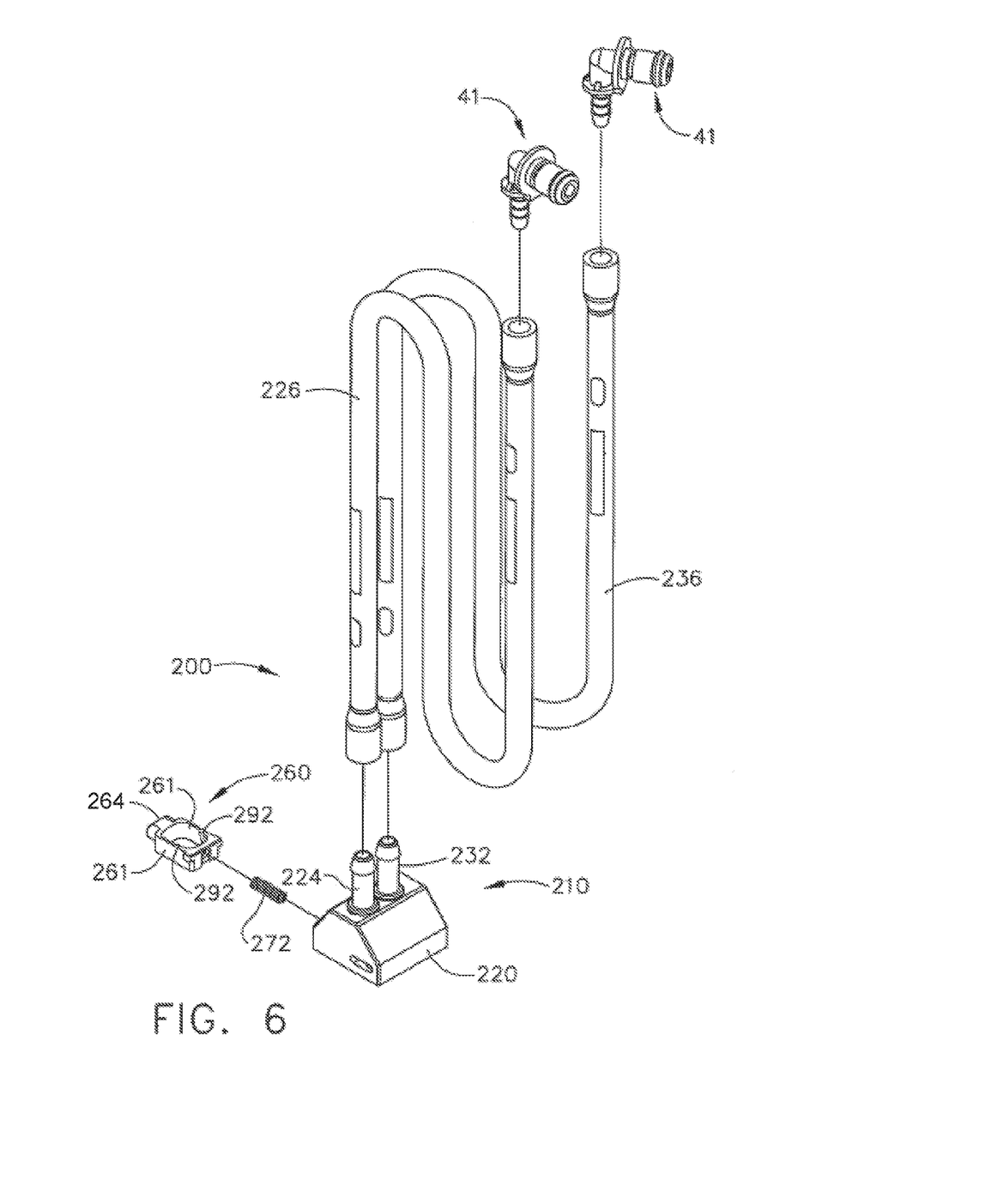
FIG. 6 is an exploded perspective view of the coupling arrangement of FIG. 5.

After an endoscope has been used, it can be reprocessed such that it can be used once again. In various circumstances, a decontamination apparatus, such as those described above, for example, can be utilized to decontaminate the endoscope and/or evaluate whether the endoscope has been properly decontaminated. In at least one circumstance, water, sterilant, and/or any other suitable fluid, can be flushed through one or more of the channels of the endoscope to remove debris, and/or any other foreign matter, which may have entered into the channels. In various embodiments, referring to FIG. 4, decontamination system 40 can include basin 14 which can be configured to receive at least a portion of an endoscope therein and, in addition, tube 42 which can, in at least one embodiment, be configured to receive at least a portion of, or be in fluid communication with, elongate portion 25 of the endoscope. In at least one embodiment, decontamination system 40 can further include circulation pump 43 which can be configured to circulate fluid from basin 14, for example, through endoscope 21 and/or tube 42, and into line 35. In certain embodiments, pump 43 can also be configured to push the fluid through heater 45 and into line 46 such that the fluid can be circulated back into basin 14, for example. In various embodiments, decontamination system 40 can further include valve 47a which can be configured to divert at least a portion of the fluid flowing within line 35 through the channels of the endoscope. More particularly, in at least one embodiment, decontamination system 40 can include six fluid connectors 41 which can be configured to receive fluid from line 35, wherein each of the six connectors 41 can be placed in fluid communication with one of the six channels of the endoscope, i.e., channels 1-6, for example, such that fluid, air, gas, etc. can flow therethrough.

Before, during, and/or after the endoscope has been subjected to a decontamination process, for example, the channels of the endoscope can be evaluated to determine whether debris, or any other foreign substance, remains in the channels. In various embodiments, referring to FIG. 4, a channel pump 4a associated with channel 4, for example, can be activated to motivate fluid through channel 4. In at least one such embodiment, a sensor, such as sensor 39, for example, can be configured to measure the flow rate of the fluid flowing through channel 4, wherein the flow rate measured by the sensor can be compared to an expected, or predicted, flow rate which represents the flow rate of the fluid when the channel is unobstructed. In various embodiments, the predicted flow rate through channel 4, for example, can be calculated in view of the parameters of channel pump 4a, the diameter, length, and/or various other properties of channel 4, and/or other features of the decontamination system. The predicted flow rate can also be empirically determined. In either event, in the event that the measured flow rate matches, or at least substantially matches, the expected flow rate, or is within a range of flow rates, for a given channel, the decontamination apparatus can convey to the operator that the existence of debris or a foreign substance within the channel is unlikely. In certain embodiments, sensors 39 can include pressure sensors which can be configured to detect the pressure of the fluid flowing through one or more channels. In the event that such a sensor 39 detects a fluid pressure that is above and/or below an expected pressure, or range or pressures, the decontamination apparatus can communicate to the operator that a foreign substance is present or that the endoscope, for example, is defective in some manner. In at least one such embodiment, the pressure sensors can, as a result, indirectly measure the rate of the fluid flowing through the channels.

FIGS. 1 and 5-10 illustrate a coupling arrangement generally designated as 200 for coupling first and second fluid coupling ports 300, 310 protruding from an endoscope 21 (FIG. 3) to corresponding ports in a decontamination device. In particular, the coupling arrangement 200 may include a connector 210 that is configured to attach to ports 300 and 310 on the endoscope proximal end 26. See FIG. 3. In various embodiments, the connector 210 may comprise a housing 220 that may be configured as shown in FIGS. 1 and 5-10. The housing portion 220 may be fabricated from any suitable material, such as Acetal, for example, and have a first fluid passage 222 extending therethrough for communication with a first hose barb 224 or other connector formation integrally protruding therefrom for attachment to a fluid conduit 226 in various known manners. In addition, the housing 220 may have a second fluid passage 230 extending therethrough in fluid communication with a second hose barb 232 or other connector formation integrally protruding therefrom for attachment to a fluid conduit 236 in various known manners. The fluid conduits 226, 236 may each comprise a flexible hose or tube and may also have a conventional hose fitting 41 attached thereto to facilitate coupling thereof to the decontamination device as was discussed above. See FIGS. 1 and 6.

Figure 7:
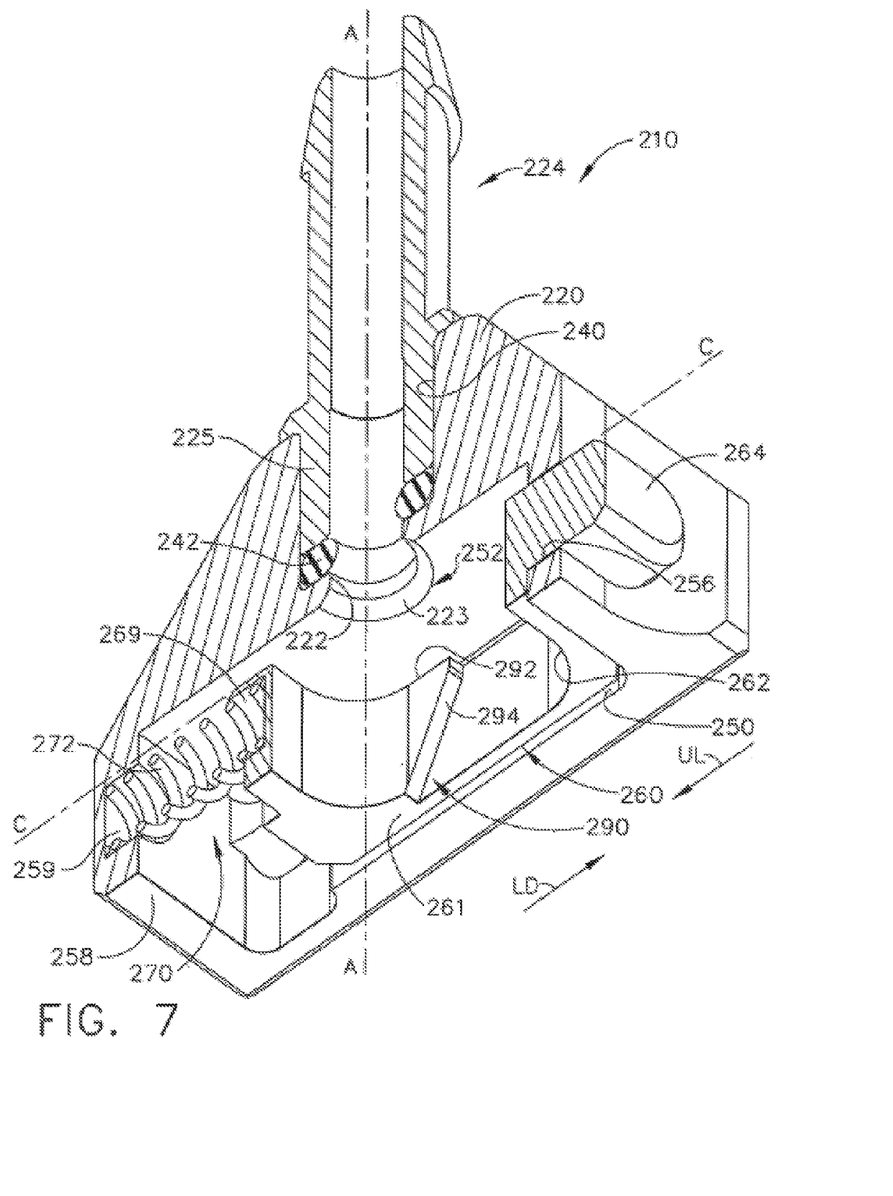
FIG. 7 is a cross-sectional view of the connector of FIG. 1 taken along line 7-7 in FIG. 1 with the latch slide in a "latched" orientation.
Figure 8:
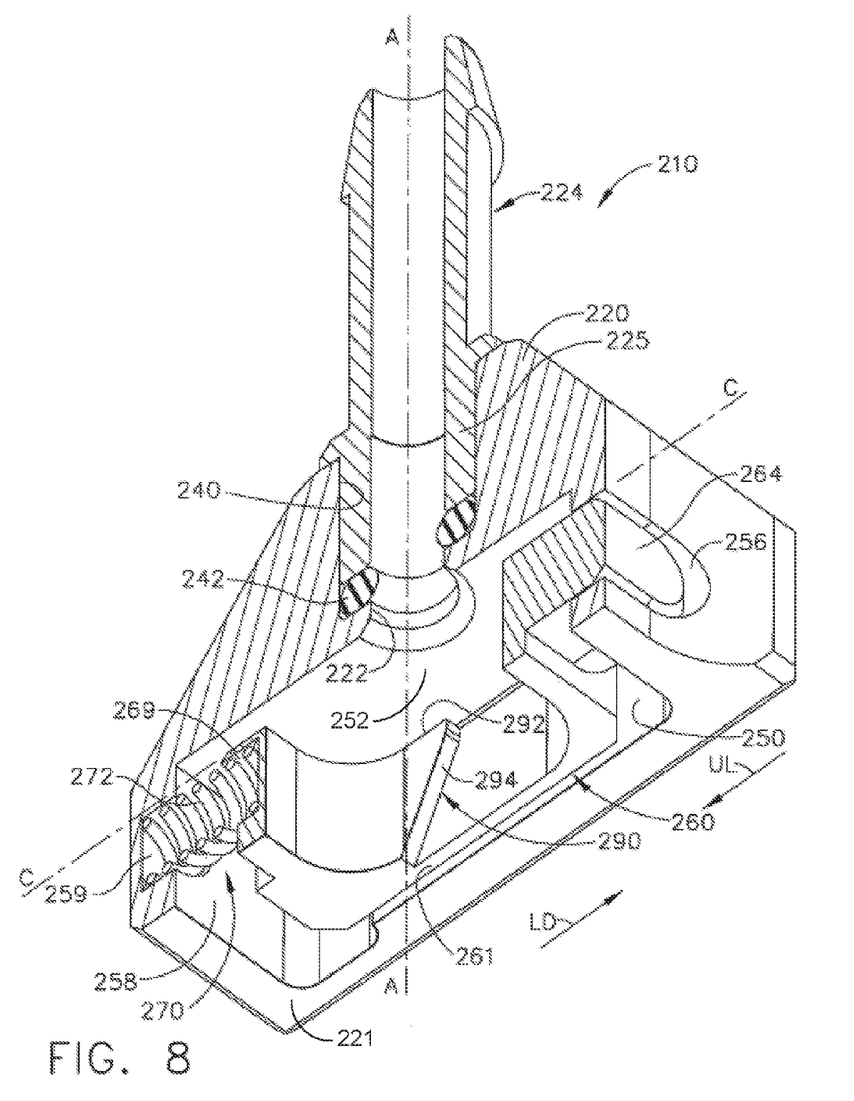
FIG. 8 is a cross-sectional view of the connector of FIG. 1 taken along line 8-8 in FIG. 1 with the latch slide in an "unlatched" orientation.

Referring to FIGS. 7 and 8, it can be observed that in various embodiments, the hose barb 224 may have an attachment end 225 that is pressed into a first attachment passage 240 that corresponds to attachment passage 222 in the housing 220. An O-ring 242 or other form of seal member may be seated in the first passage 240 to achieve a fluid-tight seal between the between attachment end 225 of the first hose barb 224 as shown. Although not specifically illustrated, the person of ordinary skill in the art will understand that the second hose barb 232 may be similarly coupled to the housing 220 such that a substantially fluid-tight seal is achieved between the second hose barb 232 and the housing 220.

Figure 1:
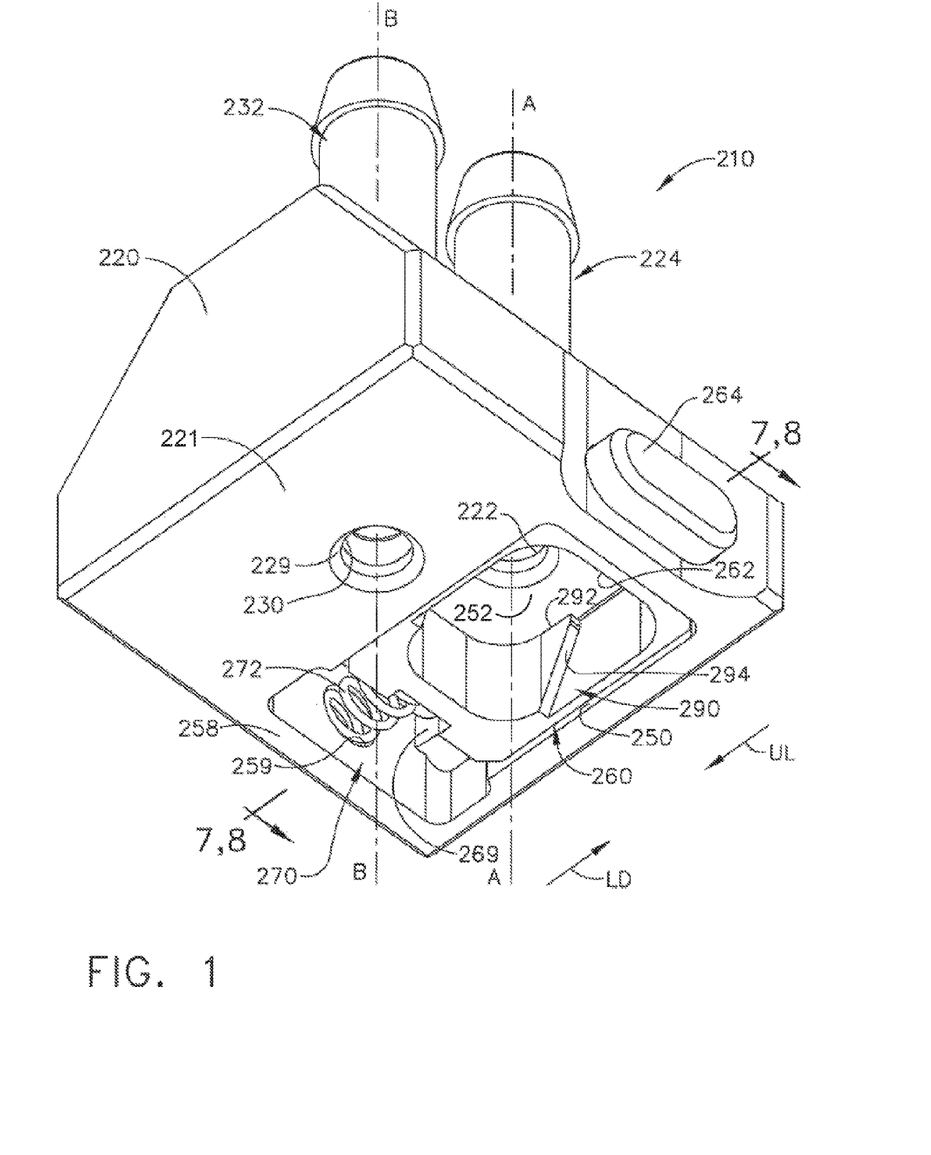
FIG. 1 is a bottom perspective view of a connector portion of the coupling arrangement of FIGS. 5 and 6.

As can also be seen in FIGS. 1, 7, and 8, in various embodiments, the housing 220 may further have a latch cavity 250 therein that is configured to slidably support a latch slide 260 therein. The latch slide 260 may have a latch opening 262 therein to provide access to the first fluid passage 222 that opens into the latch cavity 250 through the bottom surface 252 of latch cavity 250. In addition, the latch slide 260 may further have a latch button 264 that slidably extends through a button opening 256 in the housing 220. As can also be seen in FIGS. 1, 6, and 7, a biaser 270, in the form of, for example, a coil spring 272, may be positioned between an end wall 258 of the housing 220 and the latch slide 260 to bias the latch slide 260 in the latched direction represented by arrow "LD". In various embodiments, the coil spring 272 may have one end thereof seated in an opening 259 in the end wall 258 of the housing 220 and the other end of the coil spring 272 may be seated within a spring opening 269 in the latch slide 260 as can be seen in FIGS. 7 and 8.

Figure 9:
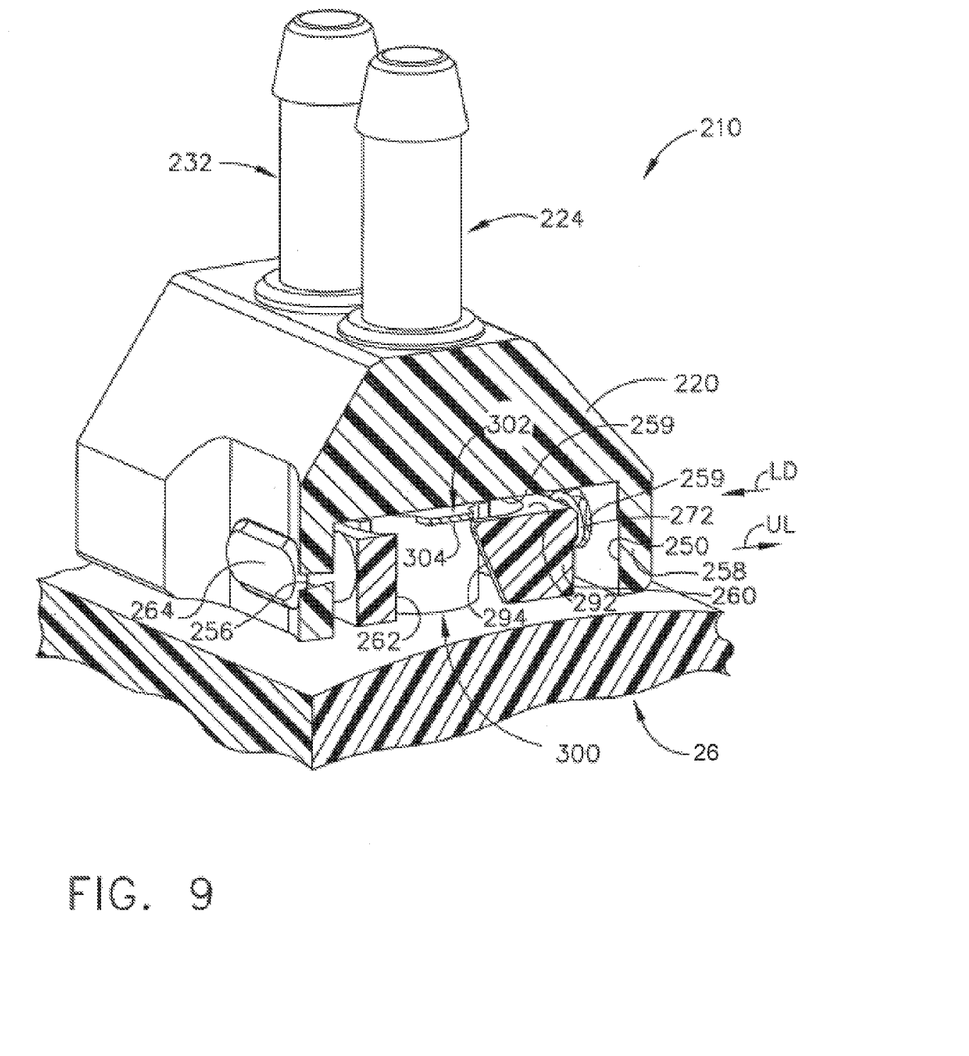
FIG. 9 is a cross-sectional view of the connector of FIGS. 1, 7, and 8 received on a portion of a medical instrument with the latch slide in the unlatched position.
Figure 10:
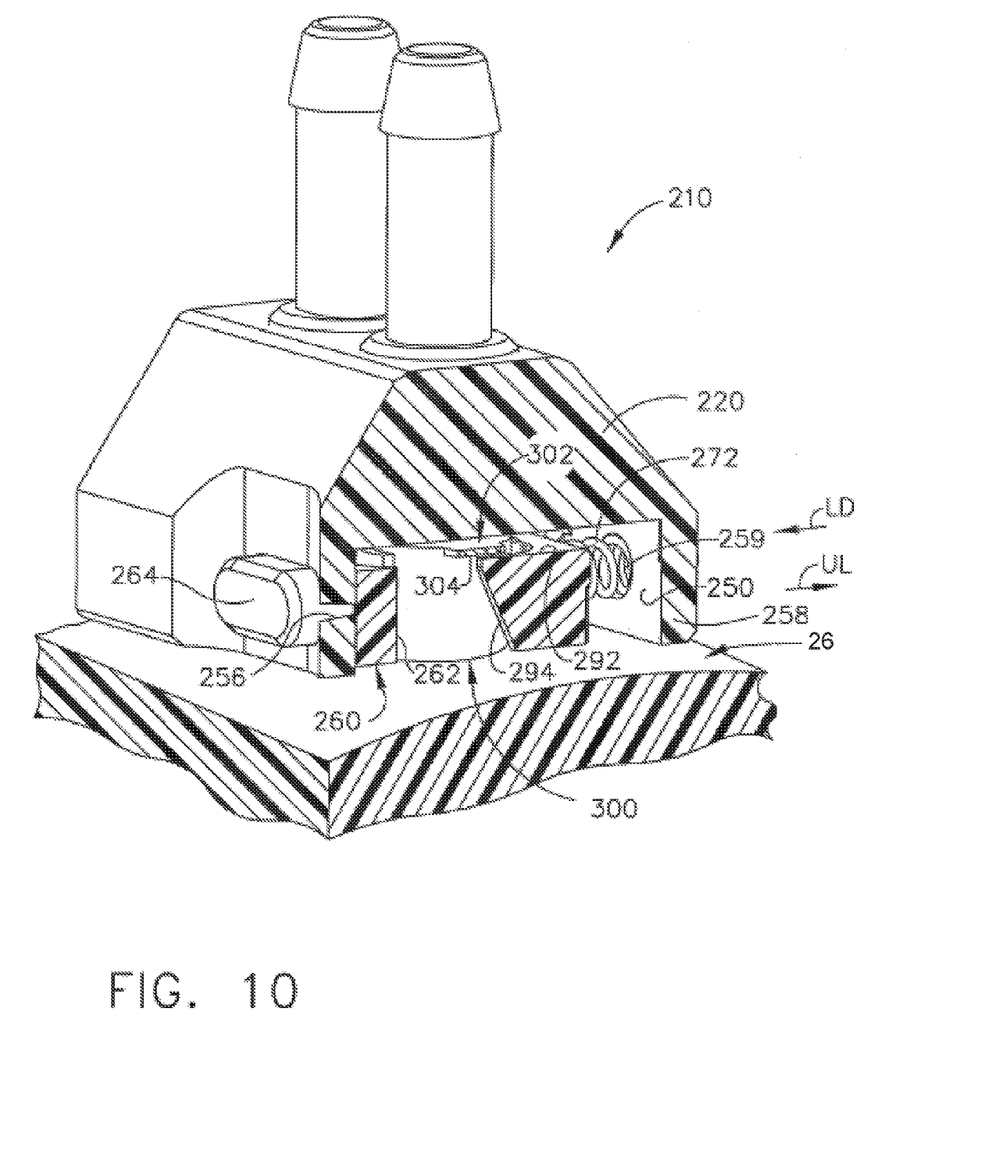
FIG. 10 is another cross-sectional view of the connector of FIGS. 1 and 7-9 received on a portion of a medical instrument with the latch slide in the latched position.

As can be seen in FIGS. 3, 9 and 10, the port 300 may have a retention feature 302 thereon. In various embodiments, the retention feature 302 may comprise a single retention flange or formation or a pair of retention flange segments 304 that protrude from opposed portions of the port 300. In still other embodiments, more than two retention segments or members could conceivably be employed. As can be seen in FIGS. 1, 7, and 8, various embodiments of the latch slide 260 may be formed with one or more latch features 290 that are configured to retainingly engage the retention features 302 on the port 300 when the latch slide 260 is in the latched position (FIGS. 7 and 10) and to disengage the retention features 302 when the latch slide 260 is biased in the unlatched direction "UL" to an unlatched position (FIGS. 8 and 9).

In various embodiments, the latch features 290 may comprise one or more ledges 292 formed or otherwise attached to the latch slide 260. For example, in arrangements wherein port 300 has two retention flange segments 304 on opposite sides of the port 300, the latch slide 260 may have a retention ledge 292 formed on opposing lateral side walls 261 thereof. See FIGS. 1 and 7. In various embodiments, one or more of the retention ledges 292 may be provided with a sloped surface, or cam surface, 294 to enable the latch slide 260 to be biased in the unlatched direction "UL" by the port 300 during attachment of the connector 210 thereto as will be discussed in further detail below.

As illustrated in FIGS. 1, 7, and 8, the first fluid passage 222 and the first hose barb 224 define a first fluid axis generally designed as axis "A-A" and the second fluid passage 230 and the second hose barb 232 define a second fluid axis generally designed as "B-B". Axes "A-A" and "B-B" may be substantially parallel to each other. As can be seen in FIGS. 7 and 8, the latch slide 260 may be positioned within the housing 220 to slide laterally along a plane defined by, for example, line "C-C" that is substantially transverse to axes "A-A" and "B-B". Also in various embodiments, the portion of the bottom surface 252 of the latch cavity 250 that is adjacent to or surrounds the first fluid passage 222 may have a chamfered or tapered surface 223 to sealingly accept an O-ring (not shown) or other seal member on port 300 or be otherwise complementarily shaped relative to the end of port 300 such that when the connector 210 is coupled to port 300, a substantially fluid-tight seal is established between port 300 and the housing 220. Similarly, a portion of the bottom surface 221 of housing 220 through which the second fluid opening 230 extends may have a chamfered portion 229 to sealingly accept an O-ring (not shown) or other seal member on port 310 or be otherwise complementarily shaped relative to the end of port 310 such that when the connector 210 is coupled to port 300, a substantially fluid-tight seal is simultaneously established between port 310 and the housing 220.

Attachment of the coupling arrangement 200 to the proximal end of the endoscope 21 may be understood from reference to FIGS. 9 and 10. FIGS. 1 and 7 illustrate the slide latch 260 in the "latched position" prior to attachment to port 300. To couple the connector 210 to port 300 of the endoscope 21 or other medical device, the connector 210 is advanced onto the port 300 such that the sloped surfaces, or cam surfaces, 294 of the latch ledges 292 are brought into contact with the retention features 302 on the port 300. Further advancement of the connector 210 causes the retention features 302 (or other portions of port 300) to ride on the sloped surfaces 294 and bias the latch slide 260 in the unlatched direction "UL" until the retention features 302 snap under or otherwise clear the ledges 290 at which point, port 300 is substantially coaxially aligned with the fluid passage 222 and port 310 is substantially coaxially aligned with fluid passage 230 in the housing 220. The biaser 270 biases the latch slide 260 in the latch direction "LD" and retains the ports 300 and 310 in substantial fluid-tight engagement with the housing 220 as shown in FIG. 10. In various embodiments, the port 300 may be otherwise complementary shaped relative to the latch opening 262 such that as port 300 is introduced therein, the interaction between the latch slide 260 and port 300 or locating portions (not shown) on port 300 causes the port 300 to be coaxially aligned with fluid passage 222 and the port 310 to be simultaneously aligned with fluid passage 230. Those of ordinary skill in the art will readily appreciate that such arrangement does not require careful alignment by the user to couple the coupling arrangement 200 to the ports 300, 310 or other adjacent ports in a medical device. In an alternative installation method, the user may elect to manually bias the slide latch 260 to the unlatched position while the port 300 is being inserted into the latch opening 262 and then release the button 264, once the port 300 has been properly seated therein. To detach the connector 210 from the ports 300, 310, the user pushes the release button 264 until the ledges 292 clear the retention features 302 to thereby permit the connector 210 to be detached from the ports 300, 310.

Thus, such arrangements have the advantage of being able to quickly couple adjacent ports on a medical instrument, such as an endoscope to a supply of fluid, such as a reprocessing unit without the use of tools and involved alignment procedures. Furthermore, although the embodiments disclosed herein have been described in connection with an endoscope, other embodiments are envisioned in connection with any suitable medical device.

Any patent, publication, application or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby. While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A endoscopic fluid line connector comprising:
   a housing comprising:
      a first fluid passage extending through the housing along a first fluid axis;
      a second fluid passage extending through the housing along a second fluid axis, wherein the second fluid axis is substantially parallel to the first fluid axis;
      a bottom surface substantially perpendicular to the second fluid axis and comprising an opening in fluid communication with the second fluid passage; and
      a latch cavity formed in the bottom surface of the housing, the latch cavity comprising a bottom surface and two opposed end walls, wherein the bottom surface of the latch cavity is off-set from the bottom surface of the housing, wherein the bottom surface of the latch cavity is substantially perpendicular to the first fluid axis and comprises an opening in fluid communication with the first fluid passage, and wherein one of the two opposed end walls comprises a button opening extending through the end wall;
   a latch slide located within the latch cavity and slidable from a latched position to an unlatched position along a lateral axis that is substantially perpendicular to the first fluid axis and the second fluid axis, the latch slide comprising:
      opposed lateral side walls that are substantially parallel to the lateral axis;
      a latch opening located between the opposed lateral side walls and extending through the latch slide in a direction substantially parallel to the first fluid axis and the second fluid axis;
      a latch button located on an end of the latch slide and positioned through the button opening in the end wall of the latch cavity; and
      a latch feature located on at least one of the two opposed lateral side walls facing the latch opening, the latch feature comprising a retention ledge located substantially parallel to the lateral axis, and a cam surface located at a non-zero angle to the lateral axis, the first fluid axis, and the second fluid axis; and
   a biaser positioned between the end wall of the latch cavity opposite the end wall comprising the button opening and the end of the latch slide opposite the end comprising the latch button.

2. The fluid line connector of claim 1, wherein the latch slide comprises two latch features, one latch feature located on each of the two opposed lateral side walls facing the latch opening, each latch feature comprising a retention ledge located substantially parallel to the lateral axis, and a cam surface located at a non-zero angle to the lateral axis, the first fluid axis, and the second fluid axis.

3. The fluid line connector of claim 1, wherein the biaser biases the latch slide toward the latched position in which the latch button extends beyond the button opening in the end wall of the latch cavity.

4. The fluid line connector of claim 1, wherein the biaser comprises a coil spring.

5. The fluid line connector of claim 4, wherein the coil spring comprises:
    a first end seated in a spring opening on the end wall of the latch cavity opposite the end wall comprising the button opening; and
    a second end seated in a spring opening on the end of the latch slide opposite the end comprising the latch button.

6. The fluid line connector of claim 1, wherein the bottom surface of the latch cavity comprises a chamfered or tapered surface surrounding the opening in fluid communication with the first fluid passage.

7. The fluid line connector of claim 1, wherein the bottom surface of the housing comprises a chamfered or tapered surface surrounding the opening in fluid communication with the second fluid passage.

8. The fluid line connector of claim 1, wherein the housing comprises an outermost surface and a recessed portion that is recessed from the outermost surface, and wherein the latch button extends through the button opening in the end wall of the latch cavity and into the recessed portion when the latch slide is in the latched position.

9. The fluid line connector of claim 8, wherein the latch button does not extend beyond the outermost surface of the housing when the latch slide is in the latched position.

10. The fluid line connector of claim 1, further comprising:
    a first hose barb protruding from the housing and in fluid communication with the first fluid passage; and
    a second hose barb protruding from the housing and in fluid communication with the second fluid passage.

11. The fluid line connector of claim 10, wherein the first hose barb comprises:
    a first attachment end connected to the first fluid passage; and
    a first coupling end configured for connecting to a first external fluid conduit; and
wherein the second hose barb comprises:
    a second attachment end connected to the second fluid passage; and
    a second coupling end configured for connecting to a second external fluid conduit.

12. The fluid line connector of claim 11, further comprising:
    a first seal member located between the first attachment end of the first hose barb and the housing; and
    a second seal member located between the second attachment end of the second hose barb and the housing.

13. The fluid line connector of claim 12, wherein the first seal member comprises a first O-ring, and wherein the second seal member comprises a second O-ring.

14. The fluid line connector of claim 10, further comprising:
    a first external fluid conduit connected to the first hose barb; and
    a second external fluid conduit connected to the second hose barb.

15. The fluid line connector of claim 14, wherein the first external fluid conduit and/or the second external fluid conduit comprise a hose fitting or a tube fitting.

16. A coupling arrangement comprising:
    the fluid line connector of claim 1; and
    a medical device coupled to the fluid line connector.

17. The coupling arrangement of claim 16, wherein the medical device comprises an endoscope.

18. The coupling arrangement of claim 17, wherein the endoscope is coupled to the fluid line connector at a proximal end of the endoscope.

19. The coupling arrangement of claim 16, wherein the medical device comprises:
    a first fluid connecting port comprising at least one retention flange; and
    a second fluid connecting port;
    wherein the latch slide is in the latched position and the retention ledge of the latch feature engages the at least one retention flange of the first fluid connecting port, thereby retaining the first fluid connecting port and the second fluid connecting port of the medical device in substantially fluid-tight engagement with the fluid line connector;
    wherein the first fluid connecting port of the medical device is in fluid communication with the first fluid passage in the housing of the fluid line connector; and
    wherein the second fluid connecting port of the medical device is in fluid communication with the second fluid passage in the housing of the fluid line connector.

20. The coupling arrangement of claim 16, wherein:
    the first fluid passage in the housing of the fluid line connector is in fluid communication with a medical device decontamination system through a first hose barb protruding from the housing and a first external fluid conduit connected to the first hose barb; and
    the second fluid passage in the housing of the fluid line connector is in fluid communication with the medical device decontamination system through a second hose barb protruding from the housing and a second external fluid conduit connected to the second hose barb.

* * * * *